United States Patent
Stover et al.

(10) Patent No.: US 10,369,227 B2
(45) Date of Patent: Aug. 6, 2019

(54) IMMUNOCOMPATIBLE POLYMERS

(71) Applicant: McMaster University, Hamilton (CA)

(72) Inventors: Harald Stover, Hamilton (CA);
Nicholas Burke, Hamilton (CA)

(73) Assignee: McMaster University, Hamilton, ON (CA)

( * ) Notice: Subject to any disclaimer, the term of this patent is extended or adjusted under 35 U.S.C. 154(b) by 14 days.

(21) Appl. No.: 14/252,137

(22) Filed: Apr. 14, 2014

(65) Prior Publication Data

US 2014/0309313 A1 Oct. 16, 2014

Related U.S. Application Data

(60) Provisional application No. 61/811,286, filed on Apr. 12, 2013.

(51) Int. Cl.
| | | |
|---|---|---|
| *A61K 47/32* | (2006.01) | |
| *A61K 47/36* | (2006.01) | |
| *A61K 9/06* | (2006.01) | |
| *A61K 9/50* | (2006.01) | |

(52) U.S. Cl.
CPC ............... *A61K 47/32* (2013.01); *A61K 9/06* (2013.01); *A61K 9/5026* (2013.01)

(58) Field of Classification Search
CPC ......... A61K 47/32; A61K 9/06; A61K 9/5026
See application file for complete search history.

(56) References Cited

U.S. PATENT DOCUMENTS

| 5,098,970 | A | * | 3/1992 | Hsieh | ................... A61L 15/60 |
|---|---|---|---|---|---|
| | | | | | 524/106 |
| 6,939,554 | B2 | * | 9/2005 | McDonald | ............ A01N 25/10 |
| | | | | | 424/405 |
| 8,071,210 | B2 | | 12/2011 | Lynn et al. | |
| 2009/0149673 | A1 | | 6/2009 | Zhang et al. | |
| 2009/0259015 | A1 | * | 10/2009 | Jiang | .................... C08F 220/26 |
| | | | | | 528/321 |
| 2011/0172315 | A1 | | 7/2011 | Matsumura et al. | |

FOREIGN PATENT DOCUMENTS

WO  WO 2010/139061  * 12/2010 ............... C08L 5/12

OTHER PUBLICATIONS

Valeur et al. (Chem. Soc. Rev. 2009, 38, 606) (Year: 2009).*
Kevin M. Zurick & Matthew Bernards 'Recent Biomedical Advances with Polyampholyte Polymers', Journal of Applied Polymer Science, 2014, DOI: 10.1002/App.40069 (1 of 9 to 9 of 9).
Shaoyi Jiang & Zhiqiang Cao, 'Ultralow-Fouling, Functionalizable, and Hydrolyzable Zwitterionic Materials and Their Derivatives for Biological Applications', Advanced Materials, 2010, 22, 920-932 DOI: 10.1002/adma.200901407.
Sarkyt E. Kudaibergenov & Alberto Ciferri, 'Natural and Synthetic Polyampholytes, 2a Functions and Applications' Macromolecular Rapid Communications. 2007, 28, 1969-1986 DOI: 10.1002/marc.200700197.
Andrew B. Lowe & Charles L. McCormick 'Synthesis and Solution Properties of Zwitterionic Polymers', Chemical Reviews, 2002, vol. 102, No. 11, 4177-4189.
Robin Rajan, Minkle Jain & Kazuaki Matsumura, 'Cryoprotective properties of completely synthetic polyampholytes via reversible addition-fragmentation chain transfer (RAFT) polymerization and the effects of hydrophobicity', Journal of Biomaterials Science, Polymer Edition, 2013 vol. 24, No. 15, 1767-1780.
Yue Huang, Zhaohui Tang, Xuefei Zhang, Haiyang Yu, Hai Sun, Xuan Pang,& Xuesi Chen 'pH-Triggered Charge-Reversal Polypeptide Nanoparticles for Cisplatin Delivery: Preparation and In Vitro Evaluation' Biomacromolecules dx.doi.org/10.1021/bm400358z pp. A-J, (2013).
Wei-Hsuan Kuo, Meng-Jiy Wang, Hsiu-Wen Chien, Ta-Chin Wei, Chiapyng Lee,& Wei-Bor Tsai 'Surface Modification with Poly(sulfobetaine methacrylate-co-acrylic acid) to Reduce Fibrinogen Adsorption, Platelet Adhesion, and Plasma Coagulation' Biomacromolecules dx.doi.org/10.1021/bm2013185 pp. 4348-4356, (2011).

* cited by examiner

*Primary Examiner* — Anna R Falkowitz
(74) *Attorney, Agent, or Firm* — Growling WLG (Canada) LLP

(57) ABSTRACT

A polymer matrix is provided comprising an amine-containing polyampholyte covalently crosslinked with an electrophilic polymer to yield an immunocompatible polymer matrix. A hydrogel system incorporating the polymer matrix is also provided.

16 Claims, 15 Drawing Sheets

IMMUNOCOMPATIBLE POLYMERS

FIELD OF THE INVENTION

The present invention generally relates to immuno-compatible polymer systems useful for cell encapsulation.

BACKGROUND OF THE INVENTION

The treatment of disease through cell encapsulation is based on entrapping hormone or enzyme producing cells within a matrix that is permeable to cell products and nutrients, while protecting the cells from the immune system. The most commonly studied capsule is the APA capsule consisting of alginate-poly-L-lysine-alginate layers. This three layer capsule consists of a calcium cross-linked alginate hydrogel core surrounded by poly-L-lysine (PLL), a polycation, and an outer coating of polyanion (alginate). The PLL layer strengthens the capsule and controls the permeability while the outer layer of polyanion is designed to reduce the high charge density of the PLL and to reduce immune reaction to the capsule itself.

These capsules pose many challenges in terms of strength and biocompatibility. To improve strength, the outer alginate layer has been replaced with reactive polymers such as poly(methyl vinyl ether-alt-maleic anhydride) ($PMM_{50}$) and poly(4,4-dimethyl-2-vinyl-2-oxazoline-5-one-co-methacrylic acid), which are capable of forming covalent cross-links with the surface bound Pa. However, the presence of high charge density PLL near the capsule surface remains a potential problem for host-compatibility. In addition, high charge density polycations are quite cytotoxic and can be detrimental to the encapsulated cells.

There have recently been attempts to improve the biocompatibility of polycations reducing the positive charge density. One approach has been to dilute or mask the positive charges of PLL by grafting PLL with poly-ethylene glycol (PEG). While this indeed reduces cytotoxicity, the PEG chains can interfere with the coating process, and regions of PLL-g-PEG may retain high local charge density. Copolymers have been developed in which the cationic monomers have been diluted using neutral hydroxy-functional comonomers, forming synthetic analogs to chitosan, a natural amine-functional polysaccharide. These charge-reduced polyamines also experience lower electrostatic complexation efficiency and a reduced ability to form covalently cross-linked networks.

It would be desirable, thus, to provide a novel polymer system that overcomes or minimizes at least one disadvantage of prior such systems.

SUMMARY OF THE INVENTION

A novel polymer matrix has now been developed which may beneficially be utilized, for example, in capsules for encapsulation of cells, therapeutics and the like. The polymer matrix comprises a primary amine-containing polyampholyte crosslinked with an electrophilic polymer that is reactive to covalently crosslink with the polyampholyte. The polymer matrix may be used as a bulk gel, or may be used to coat or to be dispersed within a hydrogel core to form a hydrogel system.

Thus, in one aspect of the present invention, a crosslinked polymer matrix is provided comprising a primary amine-containing polyampholyte covalently cross-linked with an electrophilic polymer that is reactive to covalently crosslink with the polyampholyte.

In another aspect, a method of making an immunocompatible crosslinked matrix is provided. The method comprises mixing an aqueous solution of a primary amine-containing polyampholyte with an aqueous solution of electrophilic polymer that is reactive to covalently crosslink with the polyampholyte to form an immunocompatible covalently crosslinked matrix.

In another aspect of the invention, a hydrogel system is provided comprising a primary amine-containing polyampholyte covalently crosslinked with an electrophilic polymer that is reactive to covalently crosslink with the polyampholyte to form a crosslinked polymer matrix, wherein the cross-linked matrix surrounds or is dispersed within a hydrogel core.

In another aspect, a method of making an immunocompatible hydrogel system is provided. The method comprises the steps of:

i) exposing the hydrogel to an aqueous solution comprising a primary amine-containing polyampholyte; and iii) exposing the hydrogel to an electrophilic polymer that is reactive to covalently crosslink with the polyampholyte to form an immunocompatible covalently crosslinked hydrogel system.

These and other aspects of the present invention will become apparent in the detailed description which follows by reference to the following figures.

Figure 9:
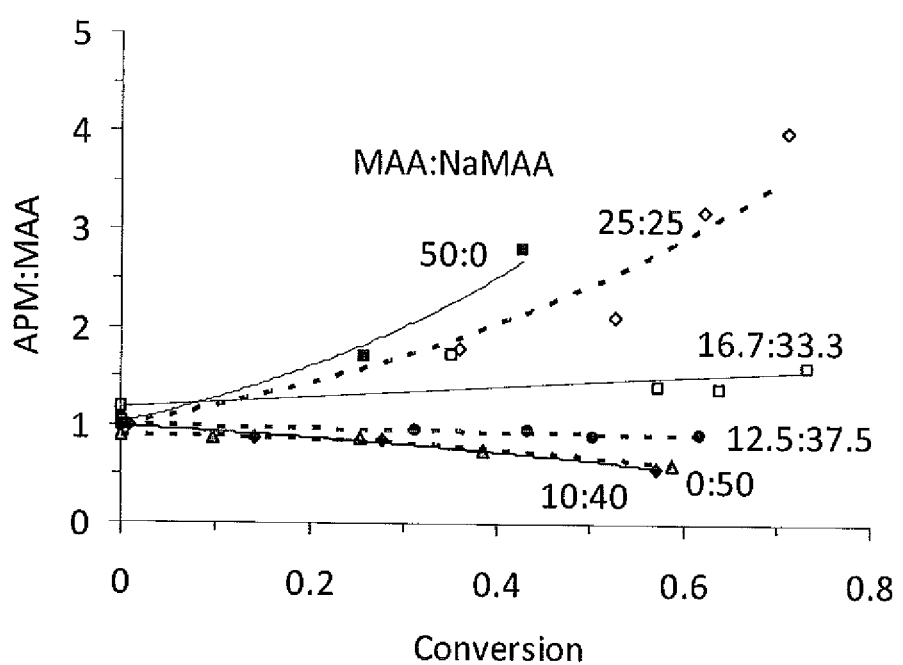

FIG. 9 illustrates the different drifts in the instantaneous APM:(MAA:NaMAA) ratios, during copolymerizations of APM, (MAA+NaMAA) and HEA with a 33.3:33.3:33.3 mol % feed ratio but with varying ratios of MAA/NaMAA.

Figure 10:
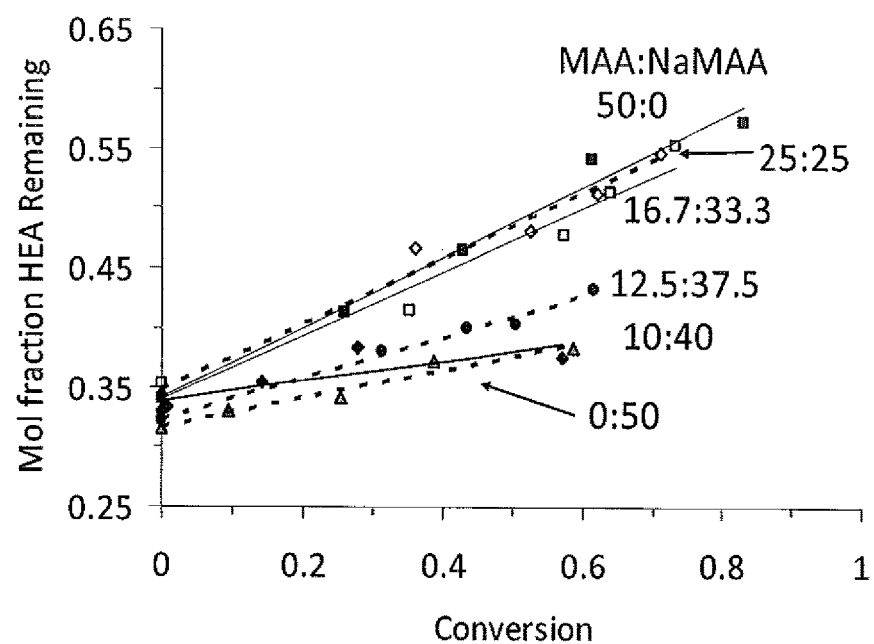
Figure 11:
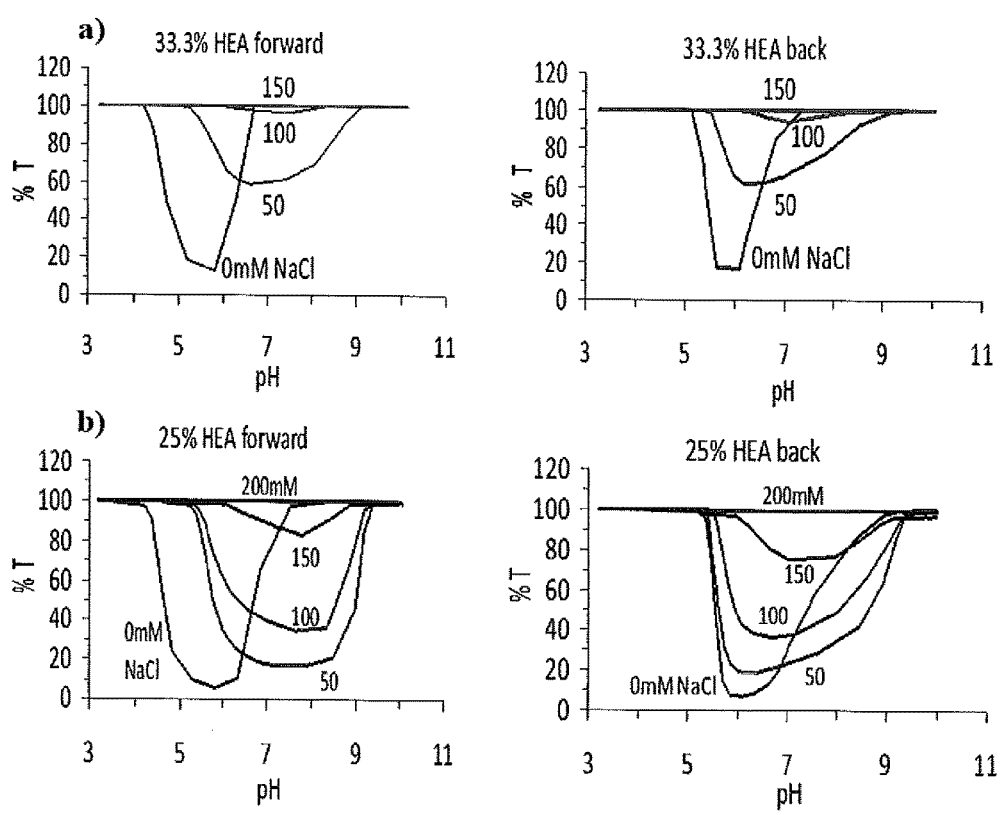
Figure 12:
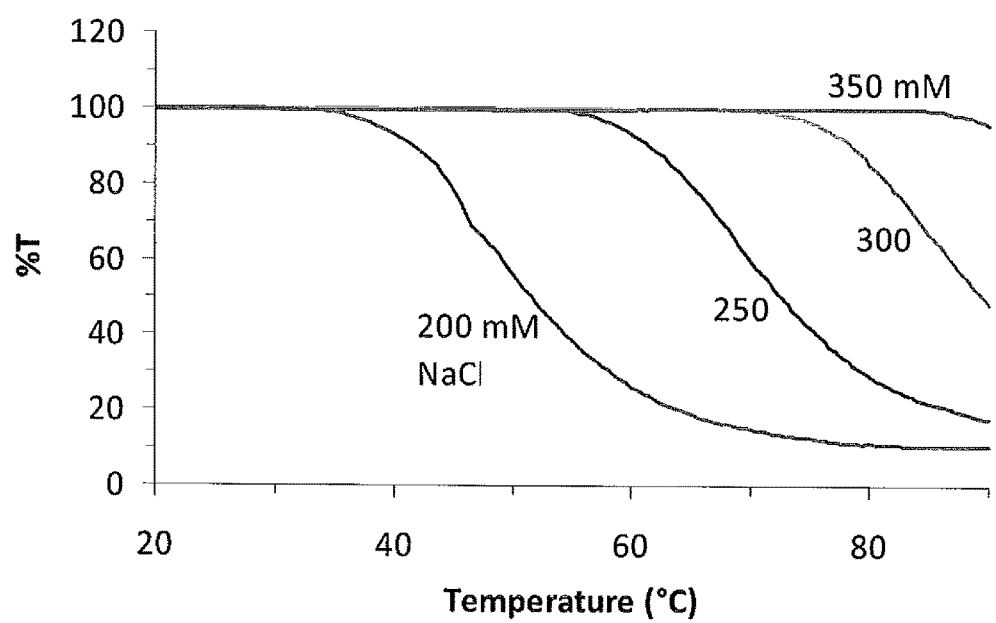

FIG. 10 graphically illustrates the molar fraction of HEA remaining in the monomer pool during copolymerization of APM, (MAA+NaMAA) and HEA with an initial 33.3:33.3: 33.3 mol % feed ratio but with varying initial ratios of MAA/NaMAA;

FIG. 11 shows turbidometric titrations of 0.1 wt % solution of APM:MAA:HEA polymers with 1:1 APM/MAA ratio and 33.3 (a) or 25 (b) mol % HEA. Both forward (with 0.1 M HCl) and backward (with 0.1 M NaOH) titrations at 21° C. in the presence of 0-200 mM NaCl are shown;

FIG. 12 shows heating curves (1° C./min) for 0.1 wt % solutions of [37.5:37.5:25] APM:MAA:HEA polymer at 200-350 mM [NaCl]. Onset of phase separation for 200, 250, 300 and 350 mM sodium chloride is at about 35° C., 59° C., 72° C. and 85° C., respectively.

Figure 13:
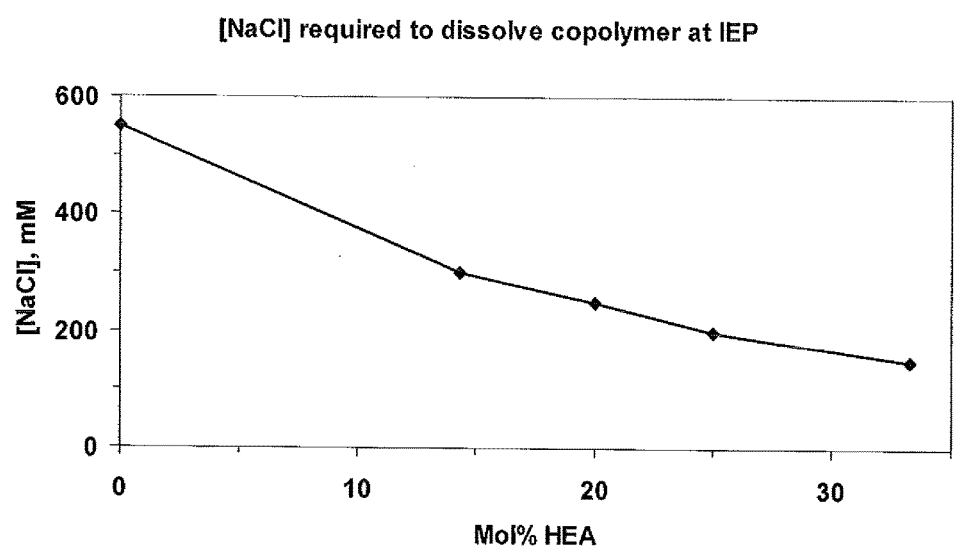
Figure 14:
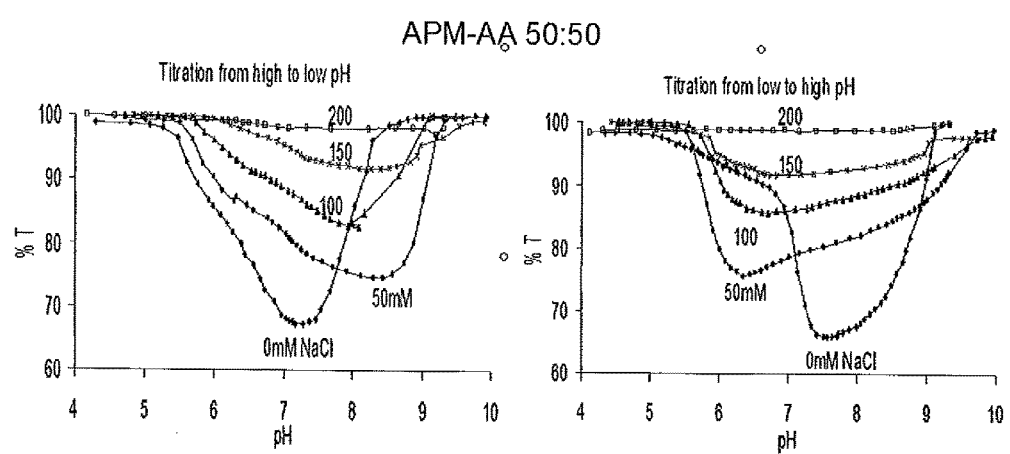

FIG. 13 shows the concentration of salt required to make the APM-MAA-HEA polymers soluble at their isoelectric point and room temperature (21° C.) as a function of HEA content in the polymers. All of the polymers have 1:1 APM/MAA ratios but varying HEA content (0-33 mol %);

FIG. 14 shows turbidometric titrations of [50:50] APM: AA polymer at 0.01 wt % titrated with dilute HCl (from high to low pH) or dilute NaOH (from low to high pH) at 21° C. in the presence of 0-200 mM NaCl. In both cases, the lowest transmittances correspond to the lowest sodium chloride concentrations.

Figure 15:
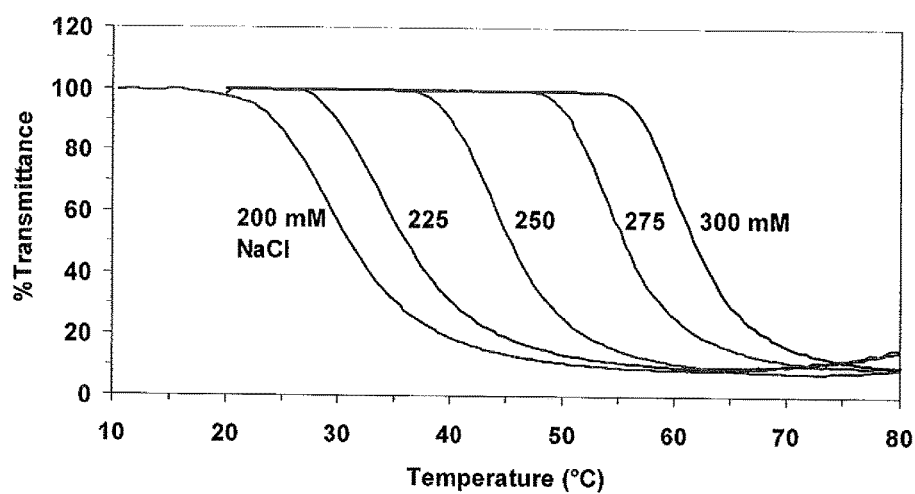

FIG. 15 shows heating curves (1° C./min) for 0.2% (2 mg/mL) solutions of [50:50] APM:AA at pH 7.5 in the presence of 200-300 mM NaCl. The onset temperature of phase separation (first decrease of transmittance) moves from about 20° C. for 200 mM sodium chloride, to about 58 C.° at 300 mM sodium chloride.

DETAILED DESCRIPTION

A novel cross-linked polymer matrix is provided comprising a primary amine-containing polyampholyte covalently cross-linked with an electrophilic monomer-containing neutral or anionic polymer.

The term "polyampholyte" is used herein to refer to zwitterionic polymers which comprise monomer units with a positive charge and monomer units with a negative charge, wherein the positive and negative charges occur on different monomer units. Polyampholytes in accordance with the present invention are polynucleophiles comprising cationic units which are primary amines. Generally, the polyampholyte may comprise about 10-90 mol % of a positively charged monomer and 90-10 mol % of a negatively charged monomer, and preferably about 30-70 mol % of a positively charged monomer and about 70-30 mol % of a negatively charged monomer. The molecular weight of suitable polyampholytes may be in the range of about 10-1000 kDa, and preferably in the range of 20-500 kDa.

Polyampholytes in accordance with the present invention may comprise monomer units with a positive charge, i.e. that become positively charged when ionized, such as N-(3-aminopropyl)methacrylamide, N-(2-aminoethyl)methacrylamide, N-(2-aminoethyl)acrylamide, 2-aminoethyl methacrylate, 2-aminoethyl acrylate, allylamine and related monomers. All of these monomers comprise primary amine groups that serve as sources of cationic charge when protonated, and that further serve as reactive groups for covalent crosslinking with electrophilic anionic or neutral reactive polymers, to form covalently crosslinked hydrogels. In addition, N-vinylacetamide and N-vinylformamide may be used as latent cationic monomers, where the primary amine is protected in the form of an amide during copolymerization, and released or yielded by hydrolysis after copolymerization.

Polyampholytes in accordance with the present invention may comprise negatively charged monomer units, i.e. that become negatively charged when ionized, such as acrylic acid (AA), methacrylic acid (MAA), 2-carboxyethyl acrylate (acrylic acid dimer), vinylbenzoic acid, N-methacryloyl-glycine and N-methacryloyl-alanine. The negatively charged monomers may also include monomers with sulfonic or phosphonic acid groups, such as vinylsulfonic acid, vinylbenzenesulfonic acid and vinylphosphonic acid.

The negatively charged monomer may also comprise a mixture of the monomer with its salt, e.g. acrylic acid combined with sodium acrylate, or methacrylic acid combined with sodium methacrylate, over the whole range of about 0% to 100% (meth)acrylic acid with 100 to 0% sodium (meth)acrylate, in order to control the copolymerization of the negatively charged monomer with the positively charged monomer, and thus allow preparation of copolymers with minimal drift in composition over the course of the radical copolymerization. This process is based on the fact that, e.g., the salt of the negatively charged monomer is generally less reactive than the uncharged acid-form of the monomer, and modifying the ratio thereof provides an effective means to achieve equal reactivities of the combined acid and salt forms of the negatively-charged monomer with the positively charged monomer during their copolymerization. As one of skill in the art will appreciate, the ratio of the negatively charged monomer and its salt may be adjusted by adjusting the solution pH through addition of acid or base, or addition of a pH buffer such as HEPES or phosphate buffer.

The polyampholyte may optionally comprise an uncharged hydrophilic monomer such as 2-hydroxyethyl methacrylate, N-(2-hydroxypropyl)methacrylamide, N-(2-hydroxyethyl)acrylamide, methoxypolyethyleneglycol methacrylate, N,N-dimethylacrylamide and acrylamide. Uncharged hydrophilic monomer may be included within the polyampholyte in an amount ranging from 10 to 90 mol %, and preferably 10 to 50 mol %, relative to the sum of the anionic and cationic monomers.

The polyampholyte may be prepared using well-established polymerization techniques in the art, for example, free radical copolymerization in aqueous solution in the presence of a suitable polymerization initiator, e.g. peroxide initiators such as potassium persulfate or water-soluble azo initiator such as Vazo-56. Other means of initiating the polymerizations known in the art include photochemical initiation, redox initiation, and initiation by ionizing radiation such as the gamma-radiation produced by a $^{60}$Co source.

The polyampholyte may also be produced by polymer modifications, e.g. to modify negatively charged monomer units within a polymer to positively charged monomer units to yield a polyampholyte. For example, a polymeric precursor such as polyacrylic acid may be reacted with ethylenediamine so as to convert a portion of the negatively charged acrylic acid units of the polymeric precursor into positively charged 2-aminoethylacrylamide units. This reaction would typically involve reaction of the polyacrylic acid with a large excess of ethylenediamine, e.g. in a ratio of ethylenediamine to acrylic acid units of 5 to 200, and preferably 10 to 50, in order to avoid or minimize crosslinking of the polyacrylic acid chains. Prior to reaction with ethylenediamine, the polyacrylic acid may optionally be activated by heating under vacuum, or another method familiar to those skilled in the art, to condense water and form cyclic anhydride units that facilitate the subsequent reaction with ethylenediamine. The reaction of the polyacrylic acid with ethylenediamine would be carried out only to an extent needed to form the desired polyampholytes.

The polyampholyte is covalently cross-linked with an electrophilic polymer, e.g. an electrophilic monomer-containing neutral polymer or anionic polymer (e.g. polyanion) that is reactive to covalently crosslink with the polyampholyte to form a polymer matrix. As will be appreciated by one of skill in the art, the electrophilic polymer may also be prepared using well-established polymerization methods as described herein.

Suitable electrophilic monomer-containing neutral or anionic reactive polymers for use to prepare the polymer matrix may have a molecular weight in the range of about 10 to 2000 kDa, more preferably in the range of 20 to about 1080 kDa, and preferably in the range of 20 to about 500 kDa. Generally, appropriate electrophilic polymers for incorporation in the cross-linked polymer matrix comprise an electrophilic monomer content in the range of about 5-80 mol %, preferably 10-50 mol %, and most preferably 20-50 mol % of the electrophilic polymer.

Suitable neutral reactive polymers include polymers prepared by copolymerization of electrophilic monomer with neutral polar monomers in an amount ranging from about 10-95 mol %, preferably 20-80 mol %, and most preferably 33-50 mol % of the electrophilic polymer. Examples of suitable neutral reactive polymers include, but are not limited to, acrylamide, N,N-dimethylacrylamide, N-(2-hydroxyethyl)acrylamide, or 2-methacryloyloxyethyl phosphorylcholine, a zwitterionic monomer, with vinylazlactones, e.g. 2-vinyl-4,4'-dimethylazlactone, N-acryloxysuccinimide, N-methacryloxysuccinimide or glycidyl methacrylate.

Suitable reactive anionic polymers include polyanions prepared by copolymerization of electrophilic monomer with anionic monomers, such as monomers having anhydride groups, in an amount ranging from about 10-95 mol %, preferably 20-80 mol %, and most preferably 33-50 mol % of the electrophilic polymer. Examples of polyanions and polyanion precursors (that become polyanions upon partial hydrolysis) for inclusion in the polymer matrix include, but are not limited to, copolymers of maleic anhydride, cyclic anhydrides such as itaconic anhydride and citraconic anhydride, and linear anhydrides such as methacrylic anhydride, with comonomers that facilitate the polymerization thereof such as alkyl vinyl ethers, e.g. methyl vinyl ether and ethyl vinyl ether, and olefins such as ethylene and propylene. Copolymers of azlactones such as vinylazlactones, e.g. 2-vinyl-4,4'-dimethylazlactone with acrylic comonomers such as acrylic acid, methacrylic acid, and optionally a third neutral comonomer such as 2-hydroxyethyl acrylate, 2-hydroxyethyl methacrylate or N-(2-hydroxypropyl)methacrylamide, N-(2-hydroxyethyl)acrylamide, acrylamide, N,N-dimethylacrylamide or 2-methacryloyloxyethylphosphorylcholine, are also appropriate polyanions, as are copolymers of N-acryloxysuccinimide, N-methacryloxysuccinimide or glycidyl methacrylate, with anionic comonomers such as acrylic and methacrylic acid.

The amount of reactive electrophilic polyanion or neutral polymer for inclusion in the polymer matrix is an amount that results in sufficient covalent crosslinking with the polyampholyte, for example, an amount corresponding to a ratio of the reactive groups on the anionic or neutral polymer, to the reactive groups on the polyampholyte, in the range of about 1:10 to 10:1, such as 3:1 to 1:3, including, for example, a ratio of the reactive groups on the anionic or neutral polymer, to the reactive groups on the polyampholyte, in the range of 2:1 to 1:2. The ratios correspond to the ratios of the moles of these matching functional groups in the mixture of polymers used to prepare the matrix. Each of the reactive polyampholyte and anionic or neutral reactive polymer may contain reactive groups corresponding to 10-90 mol % of the monomer units in the particular polymer, and preferably 30-70 mol % of the monomer units in this polymer. Individual concentrations of each of the polyampholyte, anionic or neutral polymers in the polymer mixture used to prepare the polymer matrix would be in the range of 0.1 to 20 weight %, preferably 0.5 to 10 weight %, and most preferably 1-5 weight %.

The polymer matrix is prepared as described herein by admixing aqueous solutions of the selected polyampholyte with the neutral or anionic polymer under conditions suitable for covalent cross-linking between the polymers to occur.

In another embodiment, a covalently crosslinked polymer matrix in accordance with the invention may comprise primary-amine bearing polyampholytes crosslinked by exposure to aqueous solutions of small molecule crosslinker agents, e.g. having a molecular weight less than about 1000 g/mol, such as tetrakishydroxymethylphosphonium chloride (THPC), a phosphonium salt described as being suitable for crosslinking primary amines through formation of methylene bridges.

The present crosslinked polymer matrices may be used as synthetic supports, for example, in cell studies, as well as three-dimensional matrices containing live cells for cell studies. In case of use as cell supports, the crosslinked hydrogels would be formed prior to being seeded with cells. In case of use as three-dimensional matrices the live cells would be admixed with one of the two polymer solutions used to prepare the polymer matrix, preferably the polyampholyte solution, prior to combination of the two polymer solutions to form the crosslinked polymer matrix.

In another aspect, an immuno-compatible hydrogel system is provided comprising a cross-linked polymer matrix which comprises an amine-containing polyampholyte covalently crosslinked with an electrophilic polymer that is reactive to covalently crosslink with the polyampholyte to form a polymer matrix which coats or is dispersed within a hydrogel core.

The term "hydrogel" generally refers to water soluble polymer systems capable of being gelled using biocompatible means such as divalent cation binding and thermal gellation. Examples of hydrogels that are suitable to for use in the present hydrogel system include, but are not limited to, calcium alginate, barium alginate, agarose and high viscosity gel-forming polymers such as cellulose sulphate which may be used instead of alginate, or together with alginate, as described in Prokop et al. (Adv Polym Sci 1998, 136, 1-51 and 53-73), the contents of which are incorporated herein by reference. Ionic gelling agents suitable for this purpose include calcium chloride or barium chloride.

Thus, the hydrogel of the present hydrogel system may be prepared using a water soluble polymer capable of being gelled using biocompatible means such as divalent cation binding, for example, calcium alginate and barium alginate, and thermal gellation.

The resulting gel may then be coated or admixed with an amine-containing polyampholyte to form a hydrogel-polyampholyte complex, e.g. a sodium alginate-polyampholyte solution. Suitable polyampholytes for this purpose include those as previously described. The appropriate molecular weight of a suitable polyampholyte will depend on the nature of the hydrogel, including composition, concentration and pore size of the hydrogel, as well as on the nature of the polyanion with which it will be cross-linked, including its molecular weight. Accordingly, suitable polyampholytes for use include those having a molecular weight that permit their diffusion into the hydrogel core, for example, having a molecular weight in the range of about 1-200 kDa, preferably 2-100 kDa, such as 4-15 kDa, and 15-30 kDa, and 30-60 kDa, as previously described.

The amount of polyampholyte appropriate for inclusion in the system is an amount that does not adversely affect the mechanical properties of the hydrogel core while being an amount that will result in sufficient covalent crosslinking on addition of an appropriate electrophilic monomer-containing neutral or anionic polymer reactive with the polyampholyte in the hydrogel, e.g. an amount that results in at least about a 1:1 stoichiometric functional group ratio between the polyampholyte and the polyanion. In one embodiment, a concentrated calcium alginate hydrogel bead dispersion is exposed to an amount of polyampholyte of about three times its volume at concentrations of about 0.02-1 weight/vol %, preferably 0.05 to 0.5 weight/vol %, and most preferably 0.1 to 0.2 weight/vol % solution of polyampholyte in aqueous saline or an aqueous solution containing both sodium chloride and calcium chloride. It is understood that these ratios may vary with the diameter and porosity of the hydrogel beads and possibly other factors such as the molecular weight and composition of the polyampholyte.

Following coating or admixture of the hydrogel with a polyampholyte, the hydrogel is then coated or admixed with electrophilic monomer-containing neutral or anionic polymer, as described above, that is reactive with the polyampholyte and suitable for covalent cross-linking therewith, to yield a polymer matrix coating or dispersed within the hydrogel.

The term "covalently crosslinked" as used herein with respect to a polymer matrix refers to the formation of covalent bonds between reactive polymers which are stable in the presence of an ionic solution (e.g. a sodium chloride solution at a concentration of about 1-2 M), or at high pH levels, e.g. pH 12-13, such as in the presence of 0.1 N sodium hydroxide. This is in contrast to electrostatic interactions which are commonly labile in the presence of such ionic solutions, and at high pH.

Cross-linking between the polyampholyte and the reactive neutral polymer or polyanion may occur externally to form an outer shell on the hydrogel, e.g. the outer layer or surface of the hydrogel which may generally be about 1-100 micrometer in thickness, e.g. 1-50 micrometer in thickness. To provide a hydrogel system with enhanced mechanical properties, it may be desirable to prepare the hydrogel with additional polyampholyte and polyanion coatings in order to yield an outer cross-linked shell of greater thickness, e.g. greater than 50 micrometers in thickness, higher density or greater cross-link density.

To form a hydrogel system comprising a polyampholyte cross-linked matrix within the hydrogel, the polyampholyte is added to the a hydrogel solution which is then gelled, for example in a calcium chloride gelling bath to form hydrogel beads or capsules containing polyampholyte dispersed throughout. The hydrogel beads are then immersed in a solution containing an electrophilic polymer (e.g. a reactive neutral polymer or polyanion) to form a covalently cross-linked network throughout the bead. The concentration of the polyampholyte in the hydrogel, e.g. alginate hydrogel solution, may be in the range of 0.1 to 10 weight %, preferably 0.2 to 5 weight %, and most preferably 0.5 to 2 weight %, of the hydrogel system, while the sodium alginate concentration may be in the range of about 0.5 to 2 weight % of the hydrogel system. The concentration of the reactive electrophilic polymer may be in the range of from about 0.1 to 1 weight %, and preferably 0.2-0.5 weight % of the hydrogel system.

The present hydrogel system is advantageously immuno-compatible. The term "immuno-compatible" refers to hydrogel systems which do not induce a significant immune response on administration to a host, e.g. hydrogel systems that exhibit reduced binding with endogenous host proteins. Thus, the present hydrogel system essentially lacks protein-binding sites, e.g. reactive sites capable of binding with surrounding proteins, within the crosslinked polymer matrix. This is due to the presence of a polymer matrix comprising polynucleophilic amine-containing polyampholytes that react with electrophilic reactive groups (e.g. anhydrides, reactive esters (N-hydroxysuccinimidyl, pentafluorophenyl), azlactones) within the neutral or anionic component of the matrix, to result in a matrix having a net anionic charge which is resistant to undesirable protein binding that could otherwise cause or contribute to a deleterious immune response to the hydrogel on transplant. The term "lacks" or "essentially lacks" is used herein to mean that the polymer matrix exhibits a negligible or insignificant amount of reactive protein binding sites.

While the functional groups on the reactive polyanions and reactive neutral polymers are capable of crosslinking with primary amines within the polyampholytes in order to form crosslinked networks, they may also be readily hydrolyzed into innocuous carboxylic acid anions under physiological conditions, thus removing possible attachment sites for proteins and further reducing immunogenicity of the final polymer network. The treatment or reaction to essentially eliminate or convert residual reactive groups on the hydrogel to less reactive groups may be conducted in the presence of facilitating agents. For example, the use of hydrolysis to convert residual reactive groups to less reactive groups may be facilitated by hydrolysis catalysts including certain enzymes, such as esterases, as well as tertiary amines.

The immunocompatibility of the present polymer matrix and hydrogel system is also due to the use of polyampholyte within the matrix/hydrogel. The polyampholyte contains negatively charged monomer units that provide local charge compensation for the cationically charged, primary amine-containing monomers. This effect prevents the formation of local patches with high cationic charge density that are believed to induce significant immunogenicity.

It may be desirable to provide a detectably labeled hydrogel system in order to render it trackable following its administration to a mammal, e.g. in the transplant of cells. In this regard, electrophilic reactive groups such as anhydride groups in the polyanion, may be labelled with a marker, such as a fluorescent marker, e.g. amino fluorescein, or may be modified to incorporate a chemical or biological modifier to otherwise enhance the function of the hydrogel system, for example to enhance the viability of encapsulated cells or the biocompatibility of the crosslinked network. Examples of suitable modifications include the incorporation of poly(ethylene glycol) groups by reaction of the initial polyanhydride with amino-poly(ethylene glycol), the incorporation of adhesion peptide sequences such as RGD, a tripeptide sequence consisting of arginine-glycine-aspartate, and the incorporation of spacers or other functionalities. Markers or modifiers may be added to the polyanion prior to its application to the hydrogel to engage in crosslinking.

In addition, the polymers (polyampholytes and/or neutral or anionic polymers) may be modified to customize the properties of hydrogel system. For example, the polymer may be modified to introduce macromolecules having a desirable property, including anti-inflammatory cytokines (such as IL-10 and IL-2a), or other regulatory proteins. This modification may be carried out prior to introduction of the reactive polyanion or neutral polymer to the polyampholyte, either in the formation of a polymer matrix or hydrogel system.

The present method, thus, yields a covalently crosslinked immuno-compatible hydrogel system with a reduced capacity to interact with proteins, e.g. a system that essentially lacks reactive protein binding sites and, thus, is resistant to interactions with host proteins. The cross-linked polymer matrix also functions to stabilize the system, rendering it resistant to both chemical and mechanical challenges, thereby resulting in a hydrogel system having extended implant life in a host.

The present hydrogel system has widespread utility. At the outset, the cross-linked hydrogel system per se provides a stable, biocompatible, semi-permeable membrane. Among other utilities for such membranes, that would be well-known to those of skill in the art, an immuno-compatible crosslinked hydrogel membrane in accordance with the invention is useful in biomolecular separation techniques such as ion exchange and size exclusion chromatography. In this regard, it is noted that this system is not limited to the formation of beads and/or capsules, but may also be prepared as sheets of hydrogel by spin coating or deposition on a flat surface using a spreading knife, gelling using calcium chloride and crosslinking by exposure to the polyampholyte. In this way, sheets consisting of covalently crosslinked polymer, with or without target particles such as live cells, may be prepared. In such applications, it is also possible to avoid use of alginate, and form crosslinked networks from only a bead, string or sheet of the reactive neutral or anionic polymer exposed to polyampholyte.

The present hydrogel system is also useful as a biocompatible/immuno-compatible coating on devices for implant, including, for example, stents, catheters, other medical implants and the like.

Additionally, the present immuno-compatible hydrogel system is useful as an encapsulation system for use to transplant cells for the treatment of disease, such as lysosomal storage disease (LSD), diabetes, cancer or degenerative disease such as Parkinson's, and other conditions requiring cell transplant, or to deliver other encapsulated entities to a host, including for example, therapeutic agents, enzymes and hormones. In this regard, encapsulation of a target entity may be achieved by combining the entity with the hydrogel prior to introduction of polyampholyte and/or electrophilic neutral or anionic polymer. In this regard, it is noted that the present hydrogel system may be customized in order to provide a covalently crosslinked polymer network to retain the target entity, e.g. customized to have an average pore size that exceeds the size of the target.

Embodiments of the present invention are described in the following examples which are not to be construed as limiting.

Example 1

Methods and Materials

N-(3-aminopropyl)methacrylamide hydrochloride (APM) from Polysciences and methacrylic acid (MAA, 99%), sodium methacrylate (NaMAA), N-(2-hydroxyethyl)acrylamide, ethylene carbonate (98%), 2,2'-azobis(2-methylpropionamidine) dihydrochloride (Vazo-56) and fluorescein isothiocyanate isomer 1 (FITC) from Sigma-Aldrich were used as received. N,N-Dimethylformamide (DMF, reagent grade) and methanol (reagent grade) were obtained from Caledon Laboratories (Caledon, ON). Methanol-$d_4$ and deuterium oxide ($D_2O$) were purchased from Cambridge Isotope Laboratories (Andover, Mass.). Sodium hydroxide and hydrochloric acid solutions (0.10 and 1.0 M) were obtained from LabChem Inc. Sodium alginate (Pronova UP MVG; 70% G) was purchased from NovaMatrix (Sandvika, Norway). Poly(methacrylic acid-co-4,4-dimethyl-2-vinyl-2-oxazoline-5-one) [50:50] ($PMV_{50}$) was prepared as described in Gardner and Stöver, Macromolecules 2011, 44, 7115-7123.

Optimization of APM-MAA Copolymerization

Copolymerizations were conducted at 55 or 60° C. on a 1-2 mL scale with 10% (w/v) total monomer loading, 1 mol % Vazo-56 initiator, ethylene carbonate (~1% (w/v), internal standard for NMR analysis) and appropriate amounts of NaCl or citrate buffer when needed. The samples were removed typically every 10-15 min, cooled to room temperature and analyzed by $^1$H-NMR using a Bruker Avance 200 or 600 MHz spectrometer. Conversion of the two monomers was determined from the decrease of the integrated signals representing the vinyl protons of MAA and APM. It should be noted that the chemical shifts of the MAA vinyl signals are particularly sensitive to the solution pH and care must be taken with peak assignment both before and during polymerization. Nomenclature for monomer mixtures is given as X:Y:Z, where X, Y and Z stand for mol % of APM, MAA and NaMAA, respectively. A variety of monomer mixtures were explored and several specific examples are described below.

50:12.5:37.5 comonomer mixture: In a 2 mL screw cap vial, 132.4 mg (0.743 mmol) of APM, 16 mg (0.186 mmol) of MAA along with 60.2 mg (0.557 mmol) of NaMAA were dissolved in 2 mL of 100 mM citric acid/sodium citrate buffer at pH 4.73. The total ionic strength of the buffer was adjusted to 750 mM by addition of NaCl.$^i$ Vazo-56 (4 mg, 0.0147 mmol) and ethylene carbonate (20 mg) were added and the initial pH was measured. A 100 μL aliquot diluted with 400 μL of $D_2O$ was analyzed by $^1$H NMR (600 MHz) to determine the composition of the initial monomer mixture. The vial was then heated at 60° C. and conversion was followed by NMR on similar 100 μL aliquots taken at 15, 30, 45, 60, 90 and 120 min.

75:0:25 comonomer mixture: Separate 10% (w/v) stock solutions of APM and NaMAA were prepared by adding 100 mg of monomer to 1 mL $D_2O$. In a 2 mL screw cap vial, 832 ML of 10% APM (83.2 mg, 0.467 mmol), and 168 μL of 10% NaMAA (16.8 mg, 0.155 mmol) stock solutions were combined with 1.68 mg (1 mol %) of Vazo-56 and 10 mg of ethylene carbonate. The mixture was transferred to an NMR tube and heated at 60° C. with conversion measured every 15 min.

25:45:30 comonomer mixture: A non-deuterated solvent (DMF-H$_2$O) was used for this copolymerization. In a 2 mL screw cap vial, 67.1 mg (0.780 mmol) of MAA, 77.1 mg (0.433 mmol) of APM and 56.2 mg (0.519 mmol) of NaMAA were dissolved in 2 mL of 50:50 DMF:water. The mixture was then combined with 4.7 mg (1 mol %) of Vazo-56 and 20 mg of ethylene carbonate before being heated at 60° C. Precipitation occurred during this particular polymerization so the vial was centrifuged before removing aliquots (100 µL) of the supernatant at 30, 60, 90 and 120 min that were diluted with D$_2$O before NMR analysis.

Larger scale polymerizations (1 g total monomer) were conducted using monomer ratios and conditions that had been established in the small-scale experiments except that H$_2$O was used instead of D$_2$O (Table 1). One example is described below.

TABLE 1

Preparative-scale copolymerizations[a]

| Feed Ratio APM:MAA:NaMAA | Conditions | % Conversion (isolated yield) | M$_n$ (kDa), PDI | APM:MAA (NMR) | APM:MAA (EA) |
|---|---|---|---|---|---|
| 75:0:25 | Water | 78 (75) | 33, 1.6 | 73:27 | 72:28 |
| 50:12.5:37.5 | 150 mM citrate buffer (initial pH 4.73, total ionic strength 750 mM) | 87 (75) | 10, 1.57 | 48:52 | 48:52 |
| 25:45:30 | DMF:water (50:50), Precipitation polymerization | 80 (65) | 65, 2.07 | 24:76 | 23:77 |

[a]All at 1 g scale (total monomers), 10% w/v monomer loading, 1 mol % Vazo-56 initiator, T = 55 or 60° C.

75:0:25 comonomer mixture: In a 20 mL screw cap glass vial, 832 mg (4.67 mmol) of APM, 168.3 mg (1.56 mmol) of NaMAA and 16.9 mg (0.0622 mmol) of Vazo-56 were dissolved in 10 mL of distilled water. The vial was heated at 60° C. and conversion was monitored by NMR after diluting small aliquots with D$_2$O. After 90 min, when the polymerization had reached 78% conversion, the reaction was stopped. The solution was dialyzed against distilled water using cellulose tubing (12-14 kDa MW cutoff). Freeze drying resulted in 750 mg of purified polymer. The copolymer with a 50:50 APM:(MAA+NaMAA) ratio was isolated in a similar manner except that the water used during dialysis was maintained at pH 2-3 by addition of HCl to prevent pI-related precipitation in the dialysis tubing.

GPC Analysis

The molecular weights of p(APM-co-MAA) copolymers were determined using an aqueous gel permeation chromatography (GPC) system consisting of a Waters 515 HPLC pump, Waters 717 plus autosampler, three columns (Waters Ultrahydrogel-120, -250, -500; 30 cm×7.8 mm; 6 µm particles; 0-3, 0-50, 2-300 kDa MW ranges), and a Waters 2414 refractive index detector. The mobile phase used depended on the polymer composition and IEP and was either 0.3 M NaNO$_3$ with 0.05 M phosphate buffer adjusted to pH 7 (MAA-rich copolymers) or pH 9 (50:50 copolymer), or a 1 M acetate buffer adjusted to pH 4.8 (APM-rich copolymers). The system was calibrated with polyethylene glycol) standards (Waters).

NMR Analysis $^1$H-NMR was performed using Bruker AV 200 or AV 600 spectrometers on 15 mg of isolated polymer dissolved in 1 mL of D$_2$O. The APM mol fraction was calculated by comparing the area of the APM methylene signals at 2.99 and 3.18 ppm (4H) with the area of the signals from 0.5 to 2.5 ppm (5H from MAA and 7H from APM).

Elemental Analysis

Elemental analysis was performed by the Combustion Analysis and Optical Spectroscopy facility (McMaster University) using a Therm Flash EA 1112 elemental analyzer and the carbon:nitrogen ratio was used to determine the APM:MAA ratio in the polymers.

Determination of Isoelectric Points (IEP) by Combined Potentiometric/Turbidimetric Titrations Aqueous polymer solutions (20-25 mL, 0.1-1 mg/mL) were titrated with 0.1M NaOH at ambient temperature (20-21° C.) using a PC-Titrate automatic titrator (Man-Tech, Guelph, ON) while monitoring both the pH and turbidity of the solution, using a VWR SympHony pH probe, and a Mitsubishi GT-LD photometric detector equipped with an optical fibre turbidity probe (λ>620 nm). If required, the solution pHs were adjusted prior to titration with 1 M HCl, to ensure the polymer was fully dissolved.

Study of Temperature Responsive Properties of Polyampholytes

Cloud point measurements were made using a Varian Cary 3E spectrophotometer fitted with a temperature controlled 12-sample cell holder. Copolymer solutions with a concentration of 0.2-1% (w/v) containing the desired concentration of NaCl and with a pH at the IEP were used. The temperature was ramped up or down at 1° C./min and the solution transmittance at 500 nm was measured at 0.5° C. intervals.

The same solution was subsequently manually titrated from alkaline region back to acidic region, by injecting 25 µL aliquots of 0.1 M HCl with a micropipette at a rate matching that of the initial titration, while monitoring pH and turbidity. The IEP was determined as the halfway point between the onset of turbidity in the titrations with acid and base. To determine the effect of ionic strength on the IEP, the titrations were repeated in the presence of increasing concentrations of NaCl (typically 0-500 mM) achieved by adding solid NaCl.

Fluorescently labeled P(APM-co-MAA)-f was prepared by reaction with FITC. To a 1% solution of polymer in 0.1M NaHCO$_3$ buffer (pH 9) was added 0.5 mol % of FITC (1% solution in DMF) with respect to total monomer units. The mixture was stirred for 1 hr at 21° C. and the resulting solution was dialyzed using cellulose tubing (12-14 kDa MW cutoff) against distilled water adjusted to a pH that prevented precipitation if required. The water was changed daily until the dialysate showed no detectable absorbance from DMF or fluorescein. P(APM-co-MAA)-f was isolated by freeze drying. The extent of fluorescent labeling was determined from the fluorescein absorbance at 495 nm (extinction coefficient 68,000 M$^{-1}$ cm$^{-1}$) measured by UVvisible spectroscopy (Varian Cary 50 Bio) for 0.2 wt % polymer solutions in HEPES buffered saline (pH 7.8).

Investigation of the covalent cross-linking between P(APM-co-MAA)-f [66:−34] and $PMV_{50}$ was conducted as follows. Reactive polyanion $PMV_{50}$ was dissolved in HEPES saline buffer at pH 7.8 to form a 0.2 wt % solution of the polymer. A solution of 0.2 wt % p(APM-co-MAA)-f was prepared in HEPES saline buffer and the pH was adjusted to 7.3. 50 µL of the two solutions were combined on a microscope slide to observe complexation/phase separation using fluorescent microscopy. To test the formed solid for covalent cross-linking, two drops of 0.1M NaOH were added to the microscope slide. This would deprotonate the primary amine and eliminate electrostatic interactions between p(APM-co-MAA) and $PMV_{50}$. Only covalently cross-linked polymer network would survive this NaOH challenge, while purely electrostatic complexes dissolve within seconds.

Procedure for Making Alginate-P(APM-co-MAA)-$PMV_{50}$ Capsules

The protocol described by Gardner et al. (*Langmuir,* 2010, 26, pp. 4916-4924) was used to prepare calcium alginate beads. The as-formed calcium alginate beads were washed with 1 mL 1.1% w/v $CaCl_2$, 0.45% NaCl gelling bath followed by a wash with 1 mL saline. A concentrated suspension of the resulting calcium alginate beads (460±10 µm) in saline (0.3 mL) was coated by addition of 1 mL of 0.2% p(APM-co-MAA)-f [66:34] (pH 7.3, saline) for 6 min.

The supernatant was removed and the beads were washed once with 1 mL of a solution containing 1.1 wt % $CaCl_2$ and 0.45 wt % NaCl, for 2 min. The beads were then washed with 1 mL of 0.9 wt % saline for 2 min. The resulting alginate-p(APM-co-MAA) beads were coated with 1 mL 0.2 wt % $PMV_{50}$ in 35 mM HEPES-buffered saline at pH 7.8 for 10 min. The capsules were then washed twice with 0.5 mL saline.

To test for covalent cross-linking, 2 drops of 50 mM of sodium citrate was added on the microscope slide. Sodium citrate, a good calcium chelator, liquefies the core of Ca-Alginate capsules which leaves mainly shells of alginate-p (APM-co-MAA)-$PMV_{50}$, held together by a combination of electrostatic and covalent bonds. The supernatant liquid was carefully removed and 2 drops of 0.1M NaOH was added to break the ionic interactions, and test for the presence of covalent bonds.

Results

Copolymerization Kinetics

A series of APM/MAA copolymerizations were followed by $^1$H NMR with the goal of finding conditions that gave copolymers of the desired overall composition but with a minimal drift in composition during polymerization.

Figure 1:
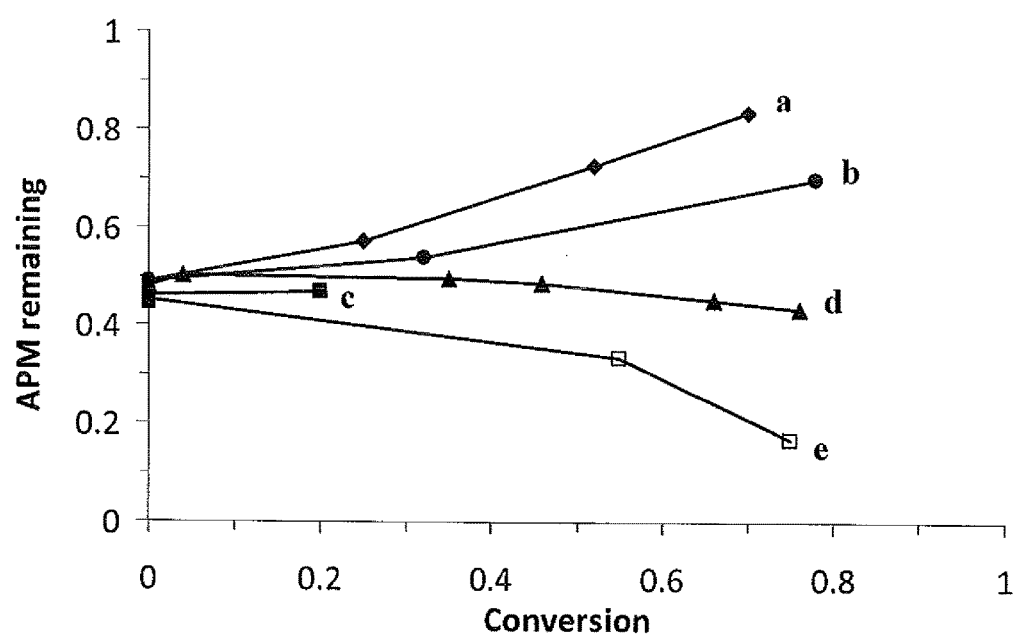
FIG. 1 shows the fraction of APM remaining in monomer mixture as a function of conversion for 50:50 APM/(MAA+NaMAA)$_{total}$ system with varying MAA/NaMAA ratios: a) 50:50:0, b) 50:25:25, c) 50:12.5:37.5, d) 50:10:40 and e) 50:0:50. Conversions were measured every 15 min during polymerization.

A series of copolymerizations with a constant 50:50 APM:(MAA+MAANa) ratio but varying MAA:NaMAA ratios followed by $^1$H NMR and the results are summarized in FIG. 1. The ratio of MAA to NaMAA in the aqueous copolymerization system may be varied by combining appropriate amounts of MM and NaMAA, or by adjusting the pH of the mixture, or by a combination of both methods. In several instances significant precipitation occurred which made it a challenge to follow the polymerizations any further. For example, during polymerization of the APM: MAA:NaMAA (50:25:25) monomer mixture, it was found that polymer precipitated within 15 min of heating at 60° C. Similar complications resulted with the APM:MAA:NaMAA (50:12.5:37.5) mixture which had precipitated by the time the conversion reached 20%.

As shown in FIG. 1, the ratio of MAA/NaMAA in the monomer mixture has a pronounced effect on the relative incorporation of MAA and APM. When only MAA is used (a 50:50:0 monomer mixture), MAA is preferentially incorporated in the polymer. The observed preference for incorporating MAA may result from electrostatic repulsion between positively charged APM.HCl monomer and the growing polymer chain, which is also positively charged. On the other hand, copolymerization of APM with NaMAA (50:0:50 monomer mix) showed preferential incorporation of APM in the polymer. These data suggested that using mixtures of MAA/NaMAA may minimize the drift in copolymer composition during polymerization.

Figure 2:
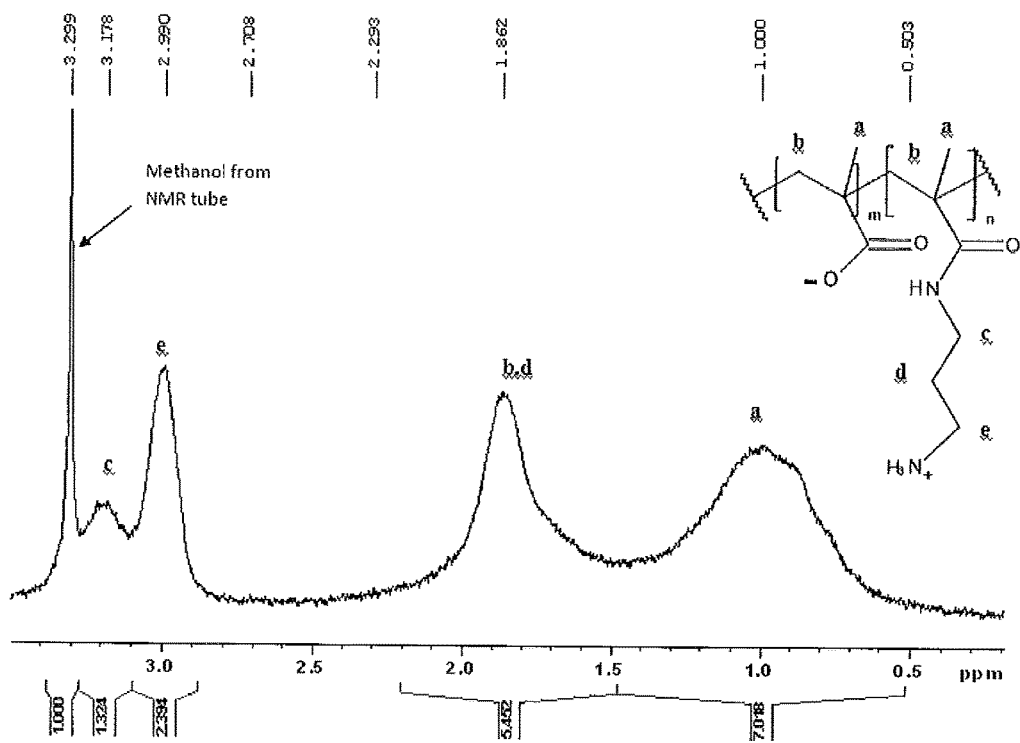
FIG. 2 shows the $^1$H NMR (200 MHz) spectra of purified poly(APM-co-MAA)

A feed ratio of 50:10:40 (APM:MAA:NaMAA) showed near stoichiometric incorporation of both monomers up to 76% conversion where precipitation occurred. It appeared that after about 70% conversion there was a preference for APM incorporation signifying onset of a small drift in composition. The drift in monomer consumption was thought to be due to a drift in solution pH that was observed by both potentiometric measurements and an upfield shift of the MAA vinyl signals in the $^1$H NMR. The drift in solution pH may be caused by a change in pKa of the functional groups once they become polymer-bound. A copolymerization done on a larger scale with a 50:10:40 monomer mixture resulted in a copolymer with a composition determined to be 51:49 APM:MAA by NMR (FIG. 2) and a molecular weight (Mn) of 32 kDa measured by GPC.

It was found that precipitation of the 51:49 APM:MAA polyampholyte was prevented in solutions having >500 mM NaCl at room temperature (FIG. 3) but higher concentrations were used during polymerization at 60 C. Copolymerization of the 50:10:40 (APM:MAA:NaMAA) monomer mixture in the presence of 750 mM NaCl remained homogeneous throughout polymerization although there was a more significant drift in relative monomer consumption (FIG. 4, curve c) than had been seen in the absence of NaCl (FIG. 1). A copolymerization using a 50:10:40 (APM:MAA: NaMAA) monomer mixture in the presence of 750 mM NaCl carried to about 65% conversion resulted in an isolated polymer with a composition determined to be [66:34] APM: MAA by elemental analysis and Mn of 40 kDa.

Figure 4:
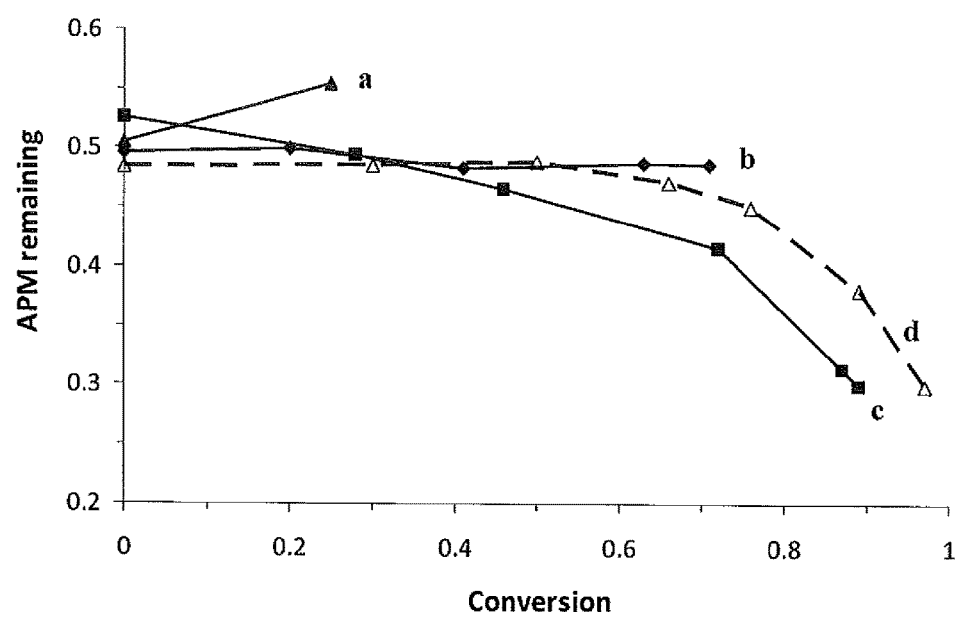
FIG. 4 shows the fraction of APM remaining in monomer mix as a function of conversion for 50:50 APM/(MAA+NaMAA)$_{total}$ system with varying MAA/NaMAA ratios in the presence of 750 mM NaCl: a) 50:25:25, b) 50:12.5:37.5, c) 50:10:40 and d) repeat of 50:12.5:37.5 carried to high conversion and monitored by 600 MHz NMR. Polymerization conditions: 10 wt % monomer loading, 750 mM NaCl in $D_2O$ with 1 mol % initiator, T=60° C.
Figure 5:
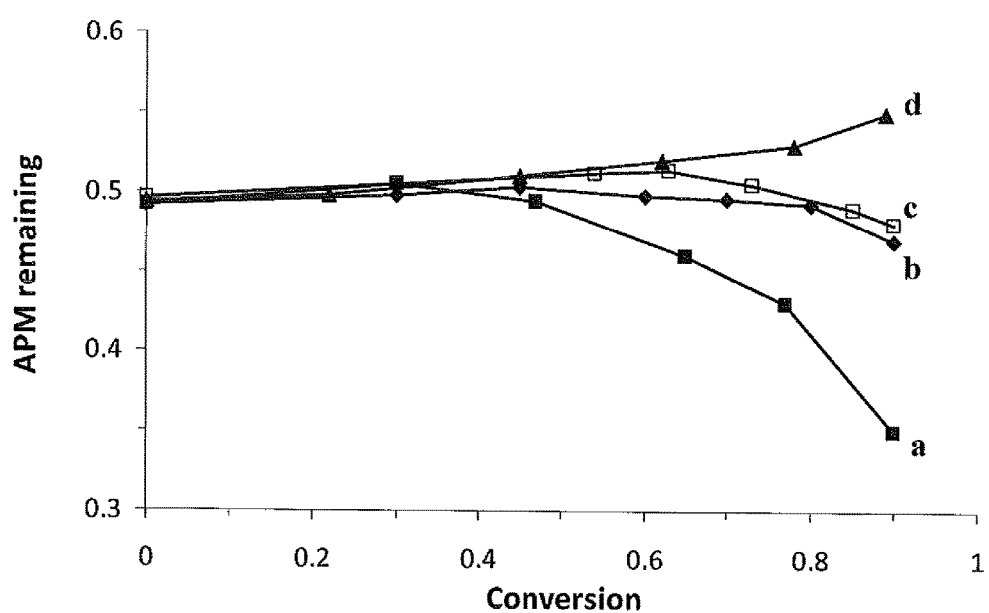
FIG. 5 shows the fraction of APM remaining in monomer mixture during polymerization of a 50:12.5:37.5 APM-MAA-NaMAA mixture in the presence of a) 0, b) 100, c) 150 or d) 200 mM citrate buffer with initial pH=4.73. Polymerization conditions: 10 wt % monomer loading, 1 mol % initiator, T=60° C., total ionic strength=750 mM.

The drift in relative monomer consumption during copolymerization was reduced by switching to a 50:12.5:37.5 (APM:MAA:NaMAA) monomer mixture (FIG. 4, curves b and d) and then further minimized by employing a 150 mM citrate buffer (initial pH 4.73) to limit pH drift during copolymerization (FIG. 5, curve c). A copolymer made using these conditions was found to have a 48:52 APM: MAA composition and Mn of 10 kDa.

Another MAA-rich copolymer was prepared using a [50:25:25] APM:MAA:NaMAA feed ratio of [50:25:25] in water but the polymerization was stopped at low conversion (32%) to avoid a broad composition distribution in the copolymer. The isolated copolymer had a [37:63] APM: MAA composition as determined by elemental analysis and Mn of 35 kDa.

A similar approach was used to prepare [75:25] APM: MAA using a feed ratio of 75:0:25 APM:MAA:NaMAA and the monomer incorporation was fairly constant throughout. A copolymer prepared using these conditions was found to have a composition of 73:27 APM:MAA by $^1$H NMR and Mn of 33 kDa.

However, attempts to prepare a [25:75] APM:MAA polyampholyte were complicated by precipitation that occurred during copolymerization for almost all comonomer ratios examined. Copolymerization of [25:75:0] and [25:0:

75] APM:MAA:NaMAA mixtures did not experience precipitation but showed pronounced preferences for incorporation of MAA and APM, respectively. Precipitation was observed with all monomer mixtures employed between [25:7.5:67.5] and [25:65:10] APM:MAA:NaMAA. Addition of NaCl up to 3 M did not prevent precipitation. The use of polar organic solvents such as methanol or DMF as cosolvents with water did make it possible to delay precipitation. A copolymerization with little or no drift in relative monomer consumption was achieved with a [25:45:30] APM:MAA:NaMAA monomer mixture in 50:50 DMF/water although there was extensive precipitation. A copolymer made using these conditions had a composition of 24:76 APM:MAA as determined by 1H NMR and Mn of 65 kDa.

Solution Properties: Titration and Effect of [NaCl]

Conformation of polyampholytes in solution not only depends on pH and composition but also on ionic strength. To test the solubility properties, the polyampholytes were titrated in 0.1% aqueous solution while monitoring the transmittance, T, of the solution. Starting at a low pH where the polyampholytes are cationic, NaOH (0.1M) was added to increase the pH and vary the charge on the polymer. Upon approaching the IEP, where positive and negative charges balance, rapid phase separation was observed for most copolymers through a sudden decrease in transmittance (increase in turbidity). Further addition of NaOH deprotonates ammonium ions, making the polymer anionic and thus soluble again. It is possible to estimate the IEP of the polyampholytes from the turbidometric titrations as the pH value half way between the clouding and clearing points.

Figure 3:
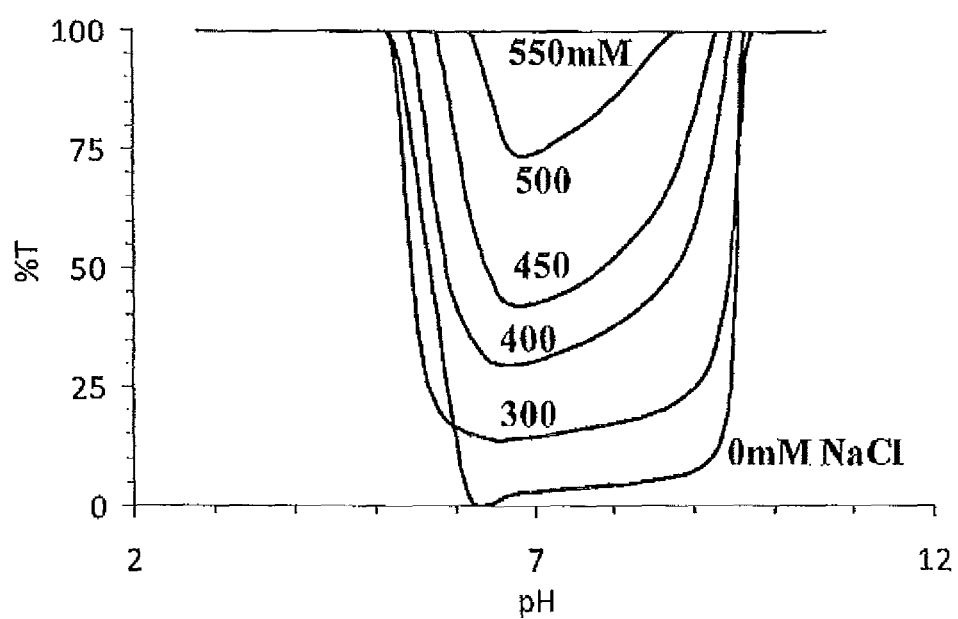
FIG. 3 shows turbidometric titration (% Transmittance vs. pH) of 0.1 wt % [50:50] APM:MAA with 0.1M NaOH at room temperature for various ionic strengths. Minima in transmittances for titrations in presence of 0, 00, 400, 450, 500 and 550 mM sodium chloride are at about 2%, 14%, 30%, 42%, 73% and 100% transmittance, respectively.

Ionic strength is known to affect polyampholyte conformation and solubility. Intra- and inter-chain electrostatic interactions are reduced at higher ionic strength which shields the opposite charges located on the polyampholyte, causing increased solubility as shown in the smaller drops in transmissivities with salt concentrations increasing from 0 to 500 mM sodium chloride. (FIG. 3).

Effect of Polyampholyte Composition on IEP

Figure 6:
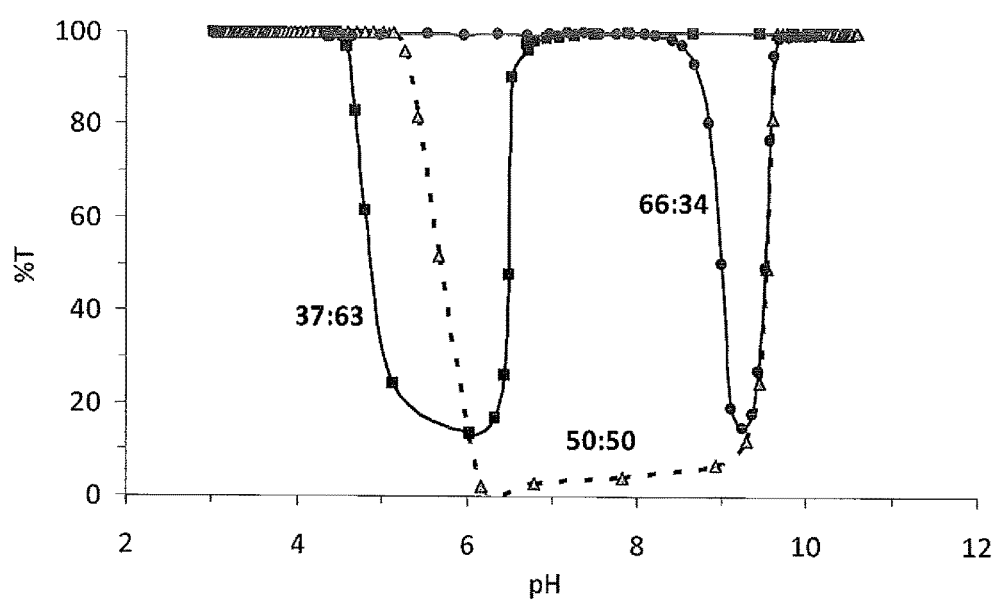
FIG. 6 shows turbidity vs. pH for the APM:MAA [37:63], [51:49] and [66:34] copolymers showing the shift of IEP with copolymer composition.

The effect of change in composition on IEP was observed through turbidometric titration of three copolymers ([51:49], [66:34], [37:63], APM:MAA) as illustrated in FIG. 6. This leads to estimates of IEP of 5.4 for the [37:63] copolymer, 6.3 for the [51:49] copolymer and 9.2 for [66:34] copolymer. Thus at physiological pH values near 7, the copolymers would have quite different natures. The [66:34] sample would be a soluble cationic polymer; the [51:49] would have a net charge close to zero and might be insoluble, while the [37:63] would be a soluble polyanion.

It is possible to predict the IEP of polyampholytes based on the composition and the pKa values of the two components. At a 1:1 ratio, the IEP is the average of the two pKas while at 2:1 and 1:2 ratios, it is simply the pKa of the major component. The three polyampholytes studied in this work have compositions that are roughly 2:1, 1:2 and 1:1 and hence might be expected to have IEP close to the pKas of APM, MAA and their average, respectively. The predicted IEPs would be roughly 10.5, 4.5 and 7.5, which are reasonably close to the measured values (9.2, 5.4 and 6.3).

Figure 7:
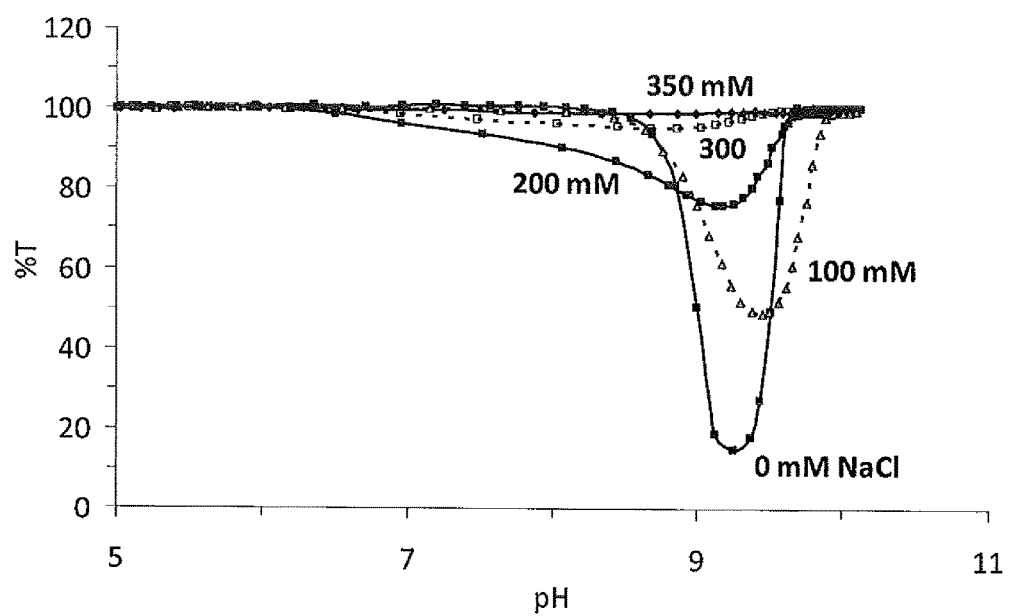
FIG. 7 shows turbidometric titration of 0.1 wt % solution of [66:34] APM:MAA polymer at 21° C. in the presence of 0-350 mM NaCl. Minima in transmittances in presence of 0, 200, 250, 300 and 350 mM sodium chloride are at about 17%, 50%, 77%, 92% and ~99% transmittance, respectively.

As had been observed with the [51:49] copolymer, increasing ionic strength made the copolymers more soluble at their IEP. The turbidometric titration (FIG. 7) of 0.1 wt % [66:34] APM:MAA with 0.1 M NaOH at 21° C. shows that the copolymer is soluble across the pH range when [NaCl] ≥350 mM.

Figure 8:
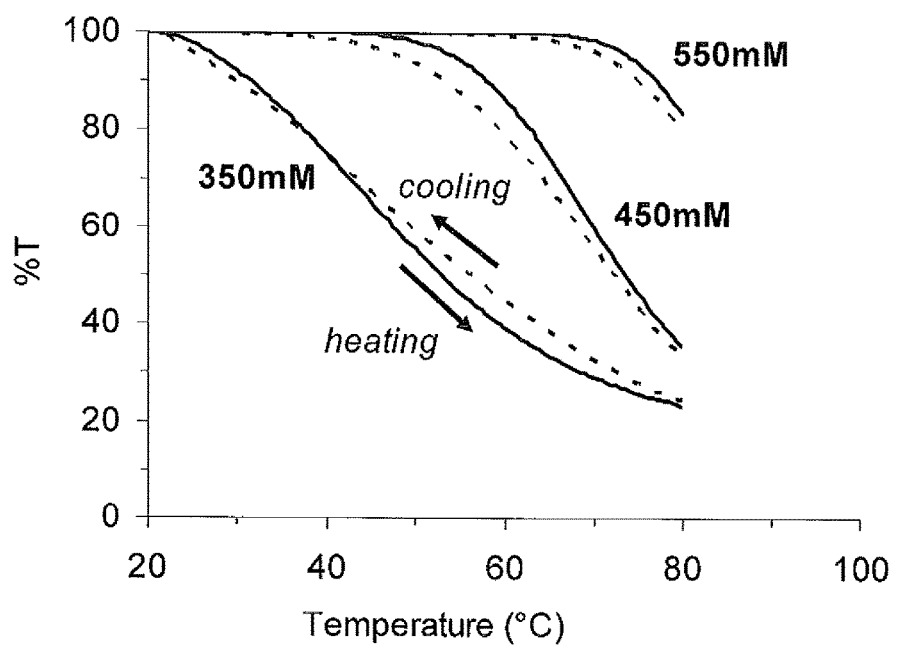
FIG. 8 shows heating and cooling curves (1° C./min) for 0.1 wt % solution of [66:34] APM:MAA polymer at 350-550 mM [NaCl]. Onset of phase separation, e.g., onset of loss of transmittance, for solutions containing 350, 450 and 550 mM sodium chloride is at about 23° C., 42° C., and 65° C., respectively.

Some of the polyampholytes proved to be temperature responsive, showing reduced solubility at higher temperatures, a common feature in amphiphilic polymers. Heating such polymers lead to desolvation of hydrophobic portions of the polymer, including ion pairs, driven by the associated entropy gain of water molecules or small ions. This process causes the polymer-polymer interactions to become dominant and leads to precipitation. To check whether the APM-MAA copolymers showed temperature responsive properties, solutions of the copolymer at IEP and salt concentrations that made the polymer soluble at room temperature were heated and then cooled while monitoring the turbidity. FIG. 8 shows the % transmittance vs. temperature curves for solutions of the [66:34] APM:MAA copolymer containing salt concentrations of 350, 450 and 550 mM with pH adjusted to IEP (9.2). All three solutions show some phase separation upon heating and then clear upon cooling with minimal hysteresis. The temperature at which phase separation occurs increases as the salt concentration increases. At these ionic strengths, increased hydrophilicity due to breaking electrostatic interactions must be greater than any desolvation of hydrophobic portions of the polymer (salting out).

Covalent Cross-Linking of P(APM-co-MAA)-f 166:341 with $PMV_{50}$

To evaluate the ability of p(APM-co-MAA) to covalently cross-link with the reactive polyanion, 0.2 wt % HEPES buffered p(APM-co-MAA)-f was combined with 0.2 wt % HEPES buffered $PMV_{50}$ on a microscope slide. The experiment was performed at pH 7.3, where the polyampholyte is cationic. At the interface between the two solutions, a solid complex was seen to form.

To confirm that the present complexation is covalent and not electrostatic, 0.1M NaOH was added to the solid complex to deprotonate primary amine on p(APM-co-MAA) and break the electrostatic interaction with the polyanion, leaving only covalent cross-links. It was observed that the complex remains and thus is covalently cross-linked.

A control experiment was performed to confirm the accuracy of cross-linked complex observed previously. P(MAA), analogous to $PMV_{50}$, is a polyanion at pH 7.3 but lacks any reactive groups. Complexation was observed when p(MAA) and p(APM-co-MAA)-f were mixed on a microscope slide. The complex appears to be liquid because it flows and aggregates into larger droplets, and syneresis is observed. After addition of 0.1M NaOH the complex dissolves indicating that the interactions were electrostatics.

To make capsules more bio and cyto-compatible, PLL the conventionally used polycation was replaced with polyampholyte. Calcium-alginate beads were coated with 0.2% HEPES buffered p(APM-co-MAA)-f[66:34] pH 7.3 at which the polymer is polycationic. Fluorescence microscopy images and confocal fluorescence microscopy images of the resulting calcium alginate capsules reveal that the polyampholyte is trapped on the surface and uniformly distributed on the beads.

The resulting capsules were then coated with 0.2% HEPES buffered $PMV_{50}$ in an attempt to form covalently cross-linked coating on the capsules. The capsule size increased due to calcium loss and confocal images confirm that the polyampholyte is still trapped on the surface of the beads.

To assess if the capsule coatings were electrostatically or covalently cross-linked, the beads were exposed to 50 mM sodium citrate which chelates the calcium and dissolves the Calcium alginate core, leaving alginate-polyampholyte-PMV electrostatic and covalent interactions. Addition of 0.1M NaOH breaks the electrostatic interaction, by deprotonating the amine groups, and leaves only amide cross-links between P(APM-co-MAA) and PMV.

Fluorescence images of these beads during the sodium citrate and sodium hydroxide test showed that Ca-Alginate beads coated with P(APM-co-MAA)-f, but not PMV, break/deflate when sodium citrate is added, and dissolve when 0.1M NaOH is subsequently added, indicating the absence of covalent crosslinking.

In contrast, Ca-Alginate-P(APM-co-MAA)-f-PMV$_{50}$ capsules form hollow capsules when challenged with sodium citrate, but these capsules survive addition of 0.1 M NaOH, indicating the presence of covalently cross-linked shells.

These results indicate that P(APM-co-MAA) is able to form both electrostatic and covalent cross-links with alginate and PMV$_{50}$ respectively at pH 7.3.

Example 2—Ternary Polyampholytes

Ternary copolymers of 3-aminopropylmethacrylamide (APM), methacrylic acid (MM) and 2-hydroxyethylacrylamide (HEA) were prepared by free radical copolymerization in water at 10 weight % total monomer loading using a cationic azo initiator. The ratio of APM and MAA was kept equimolar, while the nominal mol % HEA in the copolymerizations was varied from 14.3%, 20%, 25%, 33%.

Compositional drift between APM and MAA during these ternary copolymerizations was minimized by replacing portions of the MAA with the corresponding sodium salt (sodium methacrylate, NaMAA), in order to obtain equimolar incorporation of these two monomer types (APM, and MAA+NaMAA) during the copolymerization. This is illustrated in FIG. 9, which shows the ratio of APM:(MAA+NaMAA) in the monomer pool during copolymerizations of APM, MAA, HEA in an overall 33.3:33.3:33.3% ratio, but with MAA:NaMAA ratios ranging from 50:0, 10:40, 12.5:37.5, 25:25, 16.67:33.33, 0:50.

The mol fraction HEA remaining in the comonomer pool during these copolymerizations increases, as seen in FIG. 10, indicating preferential incorporation of the other two monomers, APM and (MAA+NaMAA), relative to HEA. This drift in composition is considered acceptable, especially for the preferred copolymerizations with initial ratios of MAA:NaMAA of 12.5:37.5.

Aqueous solutions of the resulting copolymers show pH-dependent solubilities, wherein they phase-separate due to electrostatic interactions about the region where they have zero net charge, i.e. where the polymers carry near identical amounts of cationic and anionic charges, as seen in FIG. 11. The solubility of these copolymers is also dependent on salt and temperature. Addition of salt (sodium chloride) shields the cationic and anionic charges, and improves polyampholyte solubility, such that the solubility progressively improves as more salt is added until the polymers ultimately remain in solution throughout the titration. This is seen in the decrease in turbidity of copolymer solutions with increasing salt concentrations (FIG. 12).

FIG. 13 illustrates the temperature dependence of the solubility of these copolymers at pH 7, which is close to their IEP and to physiological pH. FIG. 13 shows the turbidity curves for APM-MAA-HEA [37.5:37.5:25] in presence of 200 to 350 mM sodium chloride. The onset of turbidity is defined as the first decrease of transmission from 100% (y axis), which falls at approximately 35° C., 55° C., 72° C. and 85° C. Extrapolation to 150 mM sodium chloride suggests that this polymer will phase separate upon warming above 15-20° C., a very suitable temperature range as cell suspension are viable between 4° C. and 37° C. Hence, this polymer, and related polymers, can be thermally phase separated (deposited) upon heating from, e.g., 4° C. to 37° C., in aqueous saline at pH 7. This thermal phase separation can be used to deposit the copolymer from solution onto the bottom of multi-well plates, or onto the surface of, e.g., calcium alginate beads. This deposition leads to increased concentration of the copolymer, a feature that is very beneficial when crosslinking the copolymer with other reactive copolymers such as polyanionic polymers containing electrophilic groups such as activated esters and anhydrides, or small crosslinking molecules. Thermal phase separation can also take the place of the electrostatic attraction between reactive polyanions, such as poly(methyl vinyl ether-alt-maleic anhydride) (PMM) or poly(methacrylic acid-co-vinylazlactone) (PMV) and polycations with high charge densities such as poly-L-lysine.

FIG. 14 shows the increasing amounts of salt needed to dissolve the copolymers at their individual isoelectric point (IEP).

Example 3—APM/AA Polyampholytes

Binary copolymers of 3-aminopropylmethacrylamide (APM) and acrylic acid (AA) formed by free radical copolymerization in water as previously described and were found to have higher polarity compared to the corresponding APM/MAA copolymers. As a result, the 1:1 (molar ratio) APM:AA copolymer has solubility behaviour comparable to some of the ternary APM/MAA/HEA copolymers, as seen in FIG. 15 which shows the titration of aqueous solutions of poly(APM-co-AA) 50:50 at different salt levels by addition of either acid (from high to low pH) or base (from low to high pH). In absence of salt, the copolymer shows a pronounced region of insolubility about its IEP (black line), while at 150 mM sodium chloride (purple line), the copolymer is marginally soluble, with some turbidity. When a solution of the copolymer at pH 7.5 is heated, phase separation occurs with the phase separation temperature increasing as more salt is added. Phase separation creates a concentrated polymer phase, which is useful in a process to deposit this copolymer onto the surfaces of substrates or hydrogel beads.

Example 4—Crosslinked Gels Formed from Polyampholytes and Reactive Polyanions

Polyampholytes such as poly(APM-co-MAA), or poly (APM-co-AA), or analogous ternary copolymers incorporating a neutral polar comonomer such as HEA in addition to the cationic and anionic comonomers, may be combined directly with reactive polyanions such as PMV or PMM50 by rapid mixing to form mixed solutions that can gel by covalent crosslinking. Due to the absence of high cationic charge density in the polyampholytes, the formation of electrostatic complexes between the polyampholytes and the reactive polyanions is prevented or reduced, thereby enabling the formation of homogeneous mixed solutions which subsequently crosslink to form homogeneous gels. This process may occur in absence of alginate, and represents a route to making crosslinked bulk hydrogels.

For example, the polyampholyte, poly(APM-co-MAA) [37:63], was combined with the polyanion, A70, a copolymer comprised of 70 mol % MAA and 30 mol % 2-(methacryloyloxy)ethyl acetoacetate, to give a solution with a total polymer concentration of 5 wt % (2.5 wt % of each polymer), at a pH of 8.5 and 450 mM NaCl. The initial mixture was a clear and homogeneous solution that flowed when the vial containing the sample was inverted. After 1 hour at room temperature, the sample had gelled as evidenced by its inability to flow when the vial was inverted.

Example 5—Hydrogel-Containing Crosslinked Polyampholyte and Reactive Polyanion Matrix One consequence of the lower charge of the binary and ternary polyampholytes (cf. polycations) is their ability to be combined with polyanions such as alginate (sodium or calcium alginate) without forming the hydrophobic polyelectrolyte complexes that are formed between poly-L-lysine or other high charge density polyamines, and alginate. Specifically, this ability can allow formation of homogenous solutions (no precipitation) by combining, for example, 0.5-1 wt % of a polyampholyte of near neutral charge but still substantial amine content, e.g. poly(APM-co-MAA) 40:60 or poly(APM-co-AA) 50:50, with about 1 wt % sodium alginate, optionally containing cells. Core-cross-linked calcium alginate beads can be obtained if this solution is subsequently injected into a 100 mM calcium chloride gelling bath, to form calcium alginate beads containing polyampholyte distributed throughout the gel. Exposure of these beads to 1) solutions of reactive polyanions such as PMV or PMM50, or 2) to solutions of neutral reactive oligomers or copolymers comprising, e.g., dimethylacrylamide (DMA) and vinyldimethylazlactone (VDMA), or 3) to solutions of small molecule crosslinkers for polyamines such as tetrakis(hydroxymethyl)phosphonium chloride (THPC), leads to crosslinking of the polyampholyte within the calcium alginate carrier bead. This process permits crosslinking of calcium alginate/polyampholyte composite beads to form crosslinked beads with neutral or anionic surface charges, and no regions or "patches" of high cationic charge density. This approach is not possible using high charge density polyamines such as poly-L-lysine or poly (APM), as these polycations have strong electrostatic interactions with alginate that lead to precipitation of polyelectrolyte complexes that interfere with calcium gelation and bead formation.

What is claimed is:

1. A biocompatible cross-linked polymer matrix encapsulating live cells, said matrix comprising a primary amine-containing polyampholyte covalently cross-linked with an electrophilic polymer or a small molecule crosslinking agent that is reactive to covalently crosslink primary amine groups within the polyampholyte to result in a matrix comprising live cells and having a net neutral or anionic charge, wherein the polyampholyte lacks cationic charge dense patches because it is prepared by copolymerization of cationic primary amine-containing monomers with anionic monomers, or by modifying negatively charged monomer units in a polyanion to positively charged monomer units, or by modifying positively charged monomer units in a polycation to negatively charged monomer units, to yield a polyampholyte comprising both negatively and positively charged monomer units.

2. The polymer matrix as defined in claim 1, wherein the polyampholyte comprises monomers that yield a primary amine group selected from the group consisting of N-(3-aminopropyl)methacrylamide, N-(2-aminoethyl)methacrylamide, N-(2-aminoethyl)-acrylamide, 2-aminoethyl methacrylate, 2-aminoethyl acrylate, vinylacetamide, vinylformamide, allylamine and vinylamine.

3. The polymer matrix as defined in claim 1, wherein the polyampholyte additionally comprises an uncharged hydrophilic monomer.

4. The polymer matrix as defined in claim 3, wherein the uncharged hydrophilic monomer is selected from the group consisting of 2-hydroxyethyl methacrylate, N-(2-hydroxypropyl)methacrylamide, N-(2-hydroxyethyl)acrylamide, methoxypolyethyleneglycol methacrylate, N,N-dimethylacrylamide and acrylamide.

5. The polymer matrix as defined in claim 1, wherein the electrophilic polymer comprises an electrophilic monomer content in the range of about 5-80 mol % of the matrix in combination with reactive neutral polar monomers or anionic monomers.

6. The polymer matrix as defined in claim 5, wherein neutral polar monomer is acrylamide, N,N-dimethylacrylamide, N-(2-hydroxyethyl)acrylamide or 2-methacryloyloxyethyl phosphorylcholine.

7. The polymer matrix as defined in claim 5, wherein the electrophilic monomer combines with an anionic monomer to form a polyanion selected from copolymers of maleic anhydride, cyclic anhydrides, linear anhydrides with a comonomer selected from an alkyl vinyl ether or an olefin, copolymers of azlactone with an acrylic comonomer and optionally a third neutral comonomer, N-(2-hydroxypropyl)methacrylamide, N-(2-hydroxyethyl)acrylamide, acrylamide, N,N-dimethylacrylamide, 2-methacryloyloxyethyl-phosphorylcholine, copolymers of N-acryloxysuccinimide, N-methacryloxysuccinimide or glycidyl methacrylate with anionic acrylate comonomers.

8. The polymer matrix as defined in claim 1, wherein the small molecule crosslinking agent is a phosphonium salt.

9. An immunocompatible hydrogel system comprising a cross-linked polymer matrix as defined in claim 1, wherein the cross-linked matrix surrounds or is dispersed within a hydrogel core.

10. The hydrogel system as defined in claim 9, wherein the hydrogel core comprises alginate, agarose or cellulose sulphate alone or together with alginate.

11. The hydrogel system as defined in claim 9, wherein the polyampholyte comprises monomers that yield a primary amine group selected from the group consisting of N-(3-aminopropyl)methacrylamide, N-(2-aminoethyl)methacrylamide, N-(2-aminoethyl)acrylamide, 2-aminoethyl methacrylate, 2-aminoethyl acrylate, vinylacetamide, vinylformamide, allylamine and vinylamine.

12. The hydrogel system as defined in claim 9, wherein the electrophilic polymer comprises an electrophilic monomer content in the range of about 5-80 mol % of the polymer in combination with a neutral polar monomer selected from acrylamide, N,N-dimethylacrylamide, N-(2-hydroxyethyl) acrylamide or 2-methacryloyloxyethyl phosphorylcholine, or the electrophilic monomer combines with an anionic monomer to form a polyanion selected from copolymers of maleic anhydrides, cyclic anhydrides, linear anhydrides with a comonomer selected from an alkyl vinyl ether or an olefin, copolymers of azlactone with acrylic acid or methacrylic acid and optionally a third neutral comonomer, N-(2-hydroxypropyl)methacrylamide, N-(2-hydroxyethyl)acrylamide, acrylamide, N,N-dimethylacrylamide, 2-methacryloyloxyethyl-phosphorylcholine, copolymers of N-acryloxysuccinimide, N-methacryloxysuccinimide or glycidyl methacrylate with acrylic acid or methacrylic acid.

13. The polymer matrix as defined in claim 1, wherein the polyampholyte comprises N-(3-aminopropyl)methacrylamide and methacrylic acid, and the electrophilic polymer is poly(methacrylic acid-co-4,4-dimethyl-2-vinyl-2-oxazoline-5-one).

14. The polymer matrix of claim 1, wherein said polyampholyte comprises a positively charged monomer and a negatively charged monomer or monomer that becomes negatively charged when ionized.

15. The polymer matrix of claim 14, wherein the negatively charged monomer, or monomer that becomes negatively charged when ionized, is selected from the group consisting of acrylic acid (AA), methacrylic acid (MAA), 2-carboxyethyl acrylate, vinylbenzoic acid, N-methacryloyl-glycine, N-methacryloyl-alanine, sulfonic acid-containing monomer and phosphonic acid-containing monomer.

16. The polymer matrix as defined in claim 14, wherein the negatively charged monomer comprises a combination of the negatively charged monomer with its acid form.

* * * * *